(12) United States Patent
Hengstler (10) Patent No.: US 8,692,873 B2
(45) Date of Patent: Apr. 8, 2014

(54) VIDEO-FRAME DATA RECEIVER WITH LOW FRAME CAPTURE RATE

(75) Inventor: Stephan Hengstler, Campbell, CA (US)

(73) Assignee: Alverix, Inc., San Jose, CA (US)

(*) Notice: Subject to any disclaimer, the term of this patent is extended or adjusted under 35 U.S.C. 154(b) by 844 days.

(21) Appl. No.: 12/354,134

(22) Filed: Jan. 15, 2009

(65) Prior Publication Data

US 2010/0177176 A1    Jul. 15, 2010

(51) Int. Cl.
*H04N 7/18*    (2006.01)
(52) U.S. Cl.
USPC .... 348/61; 348/222.1; 348/440.1; 348/399.1; 382/128; 382/107
(58) Field of Classification Search
None
See application file for complete search history.

(56) References Cited

U.S. PATENT DOCUMENTS

| | | | | |
|---|---|---|---|---|
| 6,005,618 A * | 12/1999 | Fukui et al. | | 348/296 |
| 6,653,651 B1 * | 11/2003 | Meinhart et al. | | 250/573 |
| 8,023,002 B2 * | 9/2011 | Kinoshita et al. | | 348/222.1 |
| 8,446,463 B2 * | 5/2013 | Fleming et al. | | 348/61 |
| 2004/0076583 A1 * | 4/2004 | Faeldt et al. | | 424/9.2 |
| 2004/0183933 A1 * | 9/2004 | Nasu | | 348/308 |
| 2004/0257453 A1 * | 12/2004 | Lee et al. | | 348/222.1 |
| 2009/0122153 A1 * | 5/2009 | Fukui | | 348/222.1 |
| 2010/0013995 A1 * | 1/2010 | Um | | 348/500 |
| 2010/0239137 A1 * | 9/2010 | Pugia et al. | | 382/128 |
| 2010/0271479 A1 * | 10/2010 | Heydlauf | | 348/143 |
| 2013/0195332 A1 * | 8/2013 | Dylewski | | 382/128 |

* cited by examiner

*Primary Examiner* — Greg C Bengzon
(74) *Attorney, Agent, or Firm* — K&L Gates LLP (57) ABSTRACT

The present disclosure relates generally to a video frame data receiver that is capable of image acquisition at low frame rates. Such video frame data receivers may be used to capture images from diagnostic tests or assays in which lower frame capture rates are sufficient including, for example, lateral flow test strips.

37 Claims, 2 Drawing Sheets

VIDEO-FRAME DATA RECEIVER WITH LOW FRAME CAPTURE RATE

BACKGROUND

Assay test kits currently are available for testing a wide variety of medical and environmental conditions or compounds, such as a hormone, a metabolite, a toxin, or a pathogen-derived antigen. Most commonly these tests are used for medical diagnostics either for home testing, point of care testing, or laboratory use. For example, lateral flow tests are a form of immunoassay in which the test sample flows along a solid substrate via capillary action. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Readers for assays including, for example, lateral flow assays may use a camera for acquisition of images from the assay for subsequent processing and analysis. These readers may require an interface between the camera and a microcontroller that accesses images from the camera for subsequent processing and analysis. Conventional solutions of microcontroller-camera interfaces deploy a FGPA, a CPLD or a FIFO as the glue logic between the microcontroller and camera. The purpose of such glue logic is to stream images into a frame buffer located in its internal or external memory. The microcontroller can then access the image data inside the frame buffer for transmission or further processing.

SUMMARY

The present disclosure provides a video frame data receiver that is capable of image acquisition from a camera or other type of image sensor at low frame rates. Such video frame data receivers may be used to capture images indicative of the progress of diagnostic tests or assays in which slow frame capture rates are sufficient including, for example, lateral flow test strips.

The present disclosure relates to video frame data receivers that comprise at least one microprocessor; at least one signal receiver; and at least one memory device, wherein the at least one memory device stores instructions which, when executed by the at least one microprocessor, cause the at least one microprocessor to operate with the at least one signal receiver to: receive a first synchronizing signal from an image sensor in signal communication with said at least one microprocessor, said image sensor configured to store data indicative of a video frame, said first synchronizing signal indicating whether the image sensor is storing data indicative of an end of a video frame. In an embodiment, the first synchronizing signal (such as a vsync signal) is active for the duration of a capture of a video frame by an image sensor. That is, by sensing that the first synchronizing signal is active, the In a further embodiment, the instructions cause the at least one microprocessor to operate with the at least one signal receiver to receive a second synchronizing signal from the image sensor, said second synchronizing signal indicating whether the image sensor is storing data indicative of an end of one of a plurality of lines of the video frame. In an embodiment, the second synchronizing signal (such as an hsync signal) is active for the duration of a capture of a line of a video frame by an image sensor. In one embodiment, the instructions also cause the at least one microprocessor to operate with the at least one signal receiver to receive a clock signal from the image sensor, said clock signal indicating whether said image sensor is currently storing valid data indicative of at least a portion of the video frame, at a first point in time, determine whether said first synchronizing signal indicates that the image sensor is storing data indicative of the end of at least the portion of the video frame, at said first point in time, also determine whether said second synchronizing signal indicates that the image sensor is storing data indicative of the end of one of the plurality of lines of the video frame. For example, the microprocessor may determine whether both the first synchronizing signal and the second synchronizing signal are both active at the first point in time. If, at the first point in time, the first synchronizing signal indicates that the image sensor is storing data indicative of the end of the video frame and the second synchronizing signal simultaneously indicates that the image sensor is storing data indicative of the end of one of the plurality of lines of the video frame (that is, the synchronizing signals are each active, indicating that the end of a last line of a video frame has been captured), the instructions cause the microprocessor to operate with the at least one signal receiver to poll the clock signal until said clock signal indicates that said image sensor is currently storing valid data indicative of at least a portion of the video frame, and when the clock signal indicates that the image sensor is currently storing valid data indicative of at least a portion of the video frame, to read and store the then-stored data indicative of at least the portion of the video frame from the image sensor.

In an embodiment, the image sensor operates asynchronously with respect to the at least one microprocessor. For example, the image sensor may operate asynchronously with respect to the at least one microprocessor because the image sensor is in signal communication with an external oscillator. In another embodiment, the image sensor operates asynchronously with respect to the at least one microprocessor due to an external crystal. In an embodiment, the image sensor operates synchronously with respect to the at least one microprocessor by utilizing a same clock signal generator as the at least one microprocessor.

In an embodiment, the same clock signal generator is a frequency-division circuit which is in signal communication with the at least one microprocessor and the image sensor. In further embodiments, the frequency-division circuit is realized by or implemented as a pulse-width modulator or a programmable clock peripheral.

In an embodiment, the instructions cause the at least one microprocessor to poll the clock signal until said clock signal indicates that said image sensor is currently storing valid data indicative of at least a portion of the video frame by polling the clock signal until detecting at least one selected from the group consisting of a rising edge of said clock signal and falling edge of said clock signal.

In an embodiment, the video frame data receiver of the present disclosure further comprises a general purpose input/output peripheral, and the instructions cause the at least one microprocessor to operate with the general purpose input/output peripheral to read and store the then-stored data indicative of at least the portion of the video frame from the image sensor.

In an embodiment, the video frame data receiver of the present disclosure further comprises an external memory interface, and the instructions cause the at least one microprocessor to operate with the external memory interface to read and store the then-stored data indicative of at least the portion of the video frame from the image sensor. In an embodiment, the external memory interface is a separate package from the printed circuit board containing the microprocessor. In another embodiment, the external memory interface is included in a same package or on a same printed circuit board as the microprocessor—for example, the external memory interface may include an interface to on-chip memory. In certain embodiments, the external memory stores microprocessor instructions for execution by the at least one microprocessor in addition to (or instead of) storing the video frame data from the image sensor.

In an embodiment, the external memory interface enables the at least one microprocessor to communicate with at least one type of external memory unit selected from the group consisting of: a read only memory (ROM) unit, a flash memory unit, and a static random access memory (SRAM) unit. In one embodiment, wherein the external memory interface enables the at least one microprocessor to communicate with an external read only memory (ROM) unit, it should be appreciated that the external ROM unit may not be configured to store data indicative of at least a portion of a video frame. Rather, the external ROM unit may store only instructions for execution by the at least one microprocessor.

The present disclosure also relates to or provides video frame data receivers that comprise at least one microprocessor; at least one signal receiver; and at least one memory device, wherein the at least one memory device stores instructions which, when executed by the at least one microprocessor, cause the at least one microprocessor to operate with the at least one signal receiver to: receive a first synchronizing signal from an image sensor, such as a camera, in signal communication with said at least one microprocessor, said image sensor configured to store data indicative of a video frame, said first synchronizing signal indicating whether the image sensor is storing data indicative of an end of a video frame. In an embodiment, the first synchronizing signal (such as a vsync signal) is active for the duration of a capture of a video frame by an image sensor. In a further embodiment, the instructions cause the at least one microprocessor to operate with the at least one signal receiver to receive a second synchronizing signal from the image sensor, said second synchronizing signal indicating whether the image sensor is storing data indicative of an end of one of a plurality of lines of the video frame. In an embodiment, the second synchronizing signal (such as an hsync signal) is active for the duration of a capture of a line of a video frame by an image sensor. In one embodiment, the instructions also cause the at least one microprocessor to operate with the at least one signal receiver to receive a clock signal from the image sensor, said clock signal indicating whether said image sensor is currently storing valid data indicative of at least a portion of the video frame, detect an interrupt based on said clock signal, said interrupt indicating that said image sensor is currently storing valid data indicative of at least a portion of the video frame, upon detection of said interrupt, determine whether said first synchronizing signal indicates that the image sensor is storing data indicative of the end of the video frame and determine whether said second synchronizing signal indicates that the image sensor is storing data indicative of the end of one of the plurality of lines of the video frame. If, upon detection of the interrupt, the first synchronizing signal indicates that the image sensor is storing data indicative of the end of the video frame and the second synchronizing signal indicates that the image sensor is storing data indicative of the end of one of the plurality of lines of the video frame (that is, the synchronizing signals together indicate that the end of a last line of a video frame has been captured), the instructions cause the microprocessor to operate with the at least one signal receiver to read and store the then-stored data indicative of the video frame from the image sensor.

In an embodiment, the image sensor operates asynchronously with respect to the at least one microprocessor. For example, the image sensor may operate asynchronously with respect to the at least one microprocessor because the image sensor is in signal communication with an external oscillator. Alternatively, the image sensor operates asynchronously with respect to the at least one microprocessor due to the presence of an external crystal.

In an embodiment, the image sensor operates synchronously with respect to the at least one microprocessor by utilizing a same clock signal generator as the at least one microprocessor. In a further embodiment, the same clock signal generator is frequency-division circuit in signal communication with the at least one microprocessor and the image sensor. In further embodiments, the frequency-division circuit is realized by or implemented as a pulse-width modulator or a programmable clock peripheral which is in signal communication with the at least one microprocessor and the image sensor.

In an embodiment, the instructions cause the at least one microprocessor to detect an interrupt based on said clock signal by determining at least one selected from the group consisting of a rising edge and a falling edge of said clock signal.

In an embodiment, the video frame data receiver of the present disclosure further comprises a general purpose input/output peripheral, and wherein the instructions cause the at least one microprocessor to operate with the general purpose input/output peripheral to read and store the then-stored data indicative of at least the portion of the video frame from the image sensor.

In an embodiment, the video frame data receiver of the present disclosure further comprises an external memory interface, and wherein the instructions cause the at least one microprocessor to operate with the external memory interface to read and store the then-stored data indicative of either or both of at least the portion of the video frame from the image sensor or instructions for execution by the at least one microprocessor. In one embodiment, the external memory interface is a separate package from the printed circuit board containing the microprocessor. In another embodiment, the external memory interface is included in a same package or on a same printed circuit board as the microprocessor—for example, the external memory interface may include an interface to on-chip memory. In certain embodiments, the external memory stores microprocessor instructions for execution by the at least one microprocessor in addition to (or instead of) storing the video frame data from the image sensor.

In an embodiment, the external memory interface enables the at least one microprocessor to communicate with at least one type of external memory unit selected from the group consisting of: a read only memory (ROM) unit, a flash memory unit, and a static random access memory (SRAM) unit, as discussed above. In one embodiment, wherein the external memory interface enables the at least one microprocessor to communicate with an external read only memory (ROM) unit, it should be appreciated that the external ROM unit may not be configured to store data indicative of at least a portion of a video frame. Rather, the external ROM unit may store only instructions for execution by the at least one microprocessor.

The present disclosure also provides a video frame data receiver that comprises at least one microprocessor; at least one signal receiver; and at least one memory device, wherein the at least one memory device stores instructions which, when executed by the at least one microprocessor, cause the at least one microprocessor to operate with the at least one signal receiver to: receive a first synchronizing signal from the image sensor, said first synchronizing signal indicating whether the image sensor is storing data indicative of an end of one of a plurality of lines of the video frame. In an embodiment, the first synchronizing signal (such as an hsync signal) is active for the duration of a capture of a line of a video frame by an image sensor. In one embodiment, the instructions also cause the at least one microprocessor to operate with the at least one signal receiver to receive a clock signal from the image sensor, said clock signal indicating whether said image sensor is currently storing valid data indicative of at least a portion of the video frame, detect an interrupt based on said first synchronizing signal, said interrupt indicating that said image sensor is storing data indicative of the end of one of the plurality of lines of the video frame, and upon detection of said interrupt: determine whether the image sensor is currently storing valid data indicative of at least the portion of the video frame (that is, determine whether the first synchronizing signal indicates the end of a last line of a video frame has been captured). If so, the instructions cause the microprocessor to operate with the at least one signal receiver to read and store the then-stored data indicative of at least the portion of the video frame from the image sensor.

In an embodiment, the image sensor operates asynchronously with respect to the at least one microprocessor because the image sensor is in signal communication with an external oscillator.

In an embodiment, the image sensor operates synchronously with respect to the at least one microprocessor by utilizing a same clock signal generator as the at least one microprocessor. In one such embodiment, the same clock signal generator is a frequency-division circuit which is in signal communication with the at least one microprocessor and the image sensor. In further embodiments, the frequency-division circuit is realized by or implemented as a pulse-width modulator or a programmable clock peripheral in signal communication with the at least one microprocessor and the image sensor.

In an embodiment, the instructions cause the at least one microprocessor to detect an interrupt based on said first synchronizing signal by detecting at least one feature of the first synchronizing signal. For example, the microprocessor may detect an interrupt by detecting a rising edge of said first synchronizing signal or a falling edge of said first synchronizing signal.

In an embodiment, the video frame data receiver of the present disclosure further comprises a general purpose input/output peripheral, and wherein the instructions cause the at least one microprocessor to operate with the general purpose input/output peripheral to read and store the then-stored data indicative of at least the portion of the video frame from the image sensor.

In an embodiment, the instructions cause the at least one microprocessor to determine whether the image sensor is currently storing valid data indicative of at least the portion of the video frame by polling the clock signal to determine a feature of the clock signal. For example, the microprocessor may poll the clock signal to determine a data-valid edge of said clock signal. In various embodiments, the data-valid edge of the clock signal is either a rising edge of said clock signal or a falling edge of said clock signal. In an embodiment, the instructions cause the at least one microprocessor to determine whether the image sensor is currently storing valid data indicative of the video frame based on whether the clock signal is currently in a data-valid half-period.

In an embodiment, upon determining that the image sensor is currently storing valid data indicative of the video frame (such as by detecting a rising edge of the clock signal or a falling edge of the clock signal), the instructions cause the at least one microprocessor to read and store the then-stored data indicative of the video frame from the image sensor within a time period equal to less than one-half of the period of the clock signal. In another embodiment, the instructions cause the at least one microprocessor to read the data indicative of the video frame within a time period equal to less than one-half of the period of the clock signal, but storage of that data occurs within a time period exceeding one-half of the period of the clock signal. For example, the disclosed system may read and store the data within an entire clock period. It should be appreciated that any suitable timing for reading and storing may be used in various embodiments.

In an embodiment, if the image sensor is currently storing valid data indicative of the video frame, the instructions cause the at least one microprocessor to read the then-stored data indicative of the video frame only during the current data-valid half-period. The microprocessor may store the data indicative of the portion of the video frame during a period outside of the data-valid half period. For example, the at least one microprocessor may both read and store the then-stored data indicative of the video frame during an entire clock period.

The present disclosure also provides video frame data receivers that comprise at least one microprocessor; at least one signal receiver; and at least one memory device, wherein the at least one memory device stores instructions which, when executed by the at least one microprocessor, cause the at least one microprocessor to operate with the at least one signal receiver to: receive a first synchronizing signal from the image sensor, said first synchronizing signal indicating whether the image sensor is storing data indicative of an end of one of a plurality of lines of the video frame. For example, the first synchronizing signal may be a hsync signal as discussed above. In one embodiment, the microprocessor is also programmed to receive a clock signal from the image sensor, said clock signal indicating whether said image sensor is currently storing valid data indicative of at least a portion of the video frame. In one embodiment, the microprocessor detects an interrupt based on said first synchronizing signal, said interrupt indicating that said image sensor is storing data indicative of the end of one of the plurality of lines of the video frame, and upon detection of said interrupt, reads and stores the then-stored data indicative of at least the portion of the video frame from the image sensor only during the current data-valid half-period due to an alignment of said execution of said instructions with said clock signal. In a further embodiment, the microprocessor reads the data indicative of the portion of the video frame during the data-valid half period, and stores the data during a longer period, such as an entire clock period.

The present disclosure also provides a diagnostic test reader comprising an image sensor for capturing an image of a diagnostic test, said image indicating an outcome of the diagnostic test. In one embodiment, said diagnostic test is an assay test strip. In such an embodiment, the image may indicate the outcome of the diagnostic test by indicating an amount of lateral flow of an assay along said assay test strip. In one embodiment, the diagnostic test reader includes at least one microprocessor; at least one signal receiver; and at least one memory device, wherein the at least one memory device stores instructions which, when executed by the at least one microprocessor, cause the at least one microprocessor to operate with the at least one signal receiver and the at least one image sensor to: receive a first synchronizing signal (such as the hsync signals discussed above) from an image sensor in signal communication with said at least one microprocessor, said image sensor configured to store data indicative of a video frame representing said image, said first synchronizing signal indicating whether the image sensor is storing data indicative of an end of one of a plurality of lines of a video frame representing said image. The microprocessor is additionally configured to receive a clock signal from the image sensor, said clock signal indicating whether said image sensor is currently storing valid data indicative of at least a portion of the video frame. For example, the detecting a feature of the clock signal (such as rising or falling edge of the clock signal) may indicate that the image sensor is currently storing valid data. The microprocessor is also configured to detect an interrupt based on said first synchronizing signal, said interrupt indicating that said image sensor is storing data indicative of the end of one of the plurality of lines of the video frame, and upon detection of said interrupt: determine whether the image sensor is currently storing valid data indicative of at least the portion of the video frame (such as based on the clock signal). If the microprocessor determines that the image sensor is currently storing valid data indicative of at least the portion of the video frame, the microprocessor is configured to read and store the then-stored data indicative of at least the portion of the video frame from the image sensor.

In an embodiment, upon determining that the image sensor is currently storing valid data indicative of the video frame, the instructions cause the at least one microprocessor to read and store the then-stored data indicative of the video frame from the image sensor within a time period equal to less than one-half of the period of the clock signal. In a further embodiment, the microprocessor does not need to store the data indicative of at least a portion of the video frame within one-half of a clock period. In this embodiment, the microprocessor can read the data indicative of at least a portion of the video frame within the one-half clock period, and can read and store the data within a full clock period. In another embodiment, the microprocessor is programmed to both read and store the data indicative of at least the portion of the video frame within one-half of a clock period.

Additional features and advantages are described herein, and will be apparent from, the following Detailed Description.

DETAILED DESCRIPTION

Figure 1:
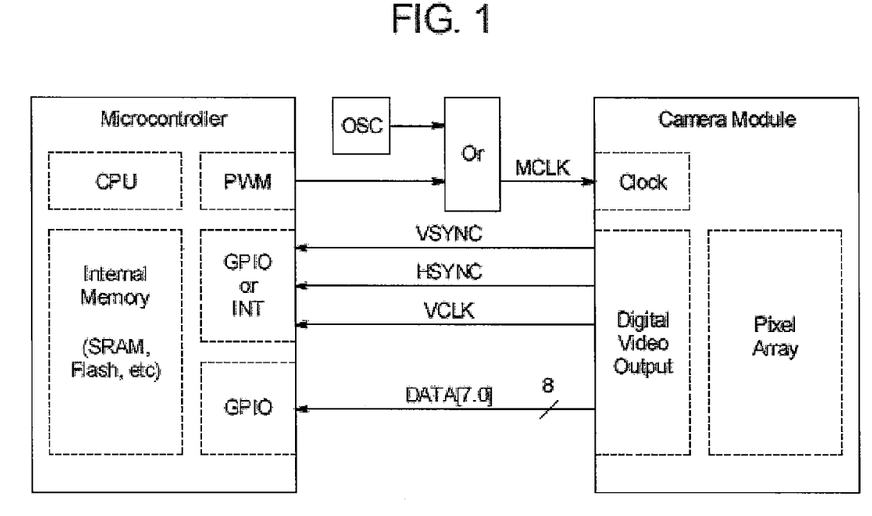
FIG. 1 shows a block diagram of the microcontroller-camera interface.
Figure 2:
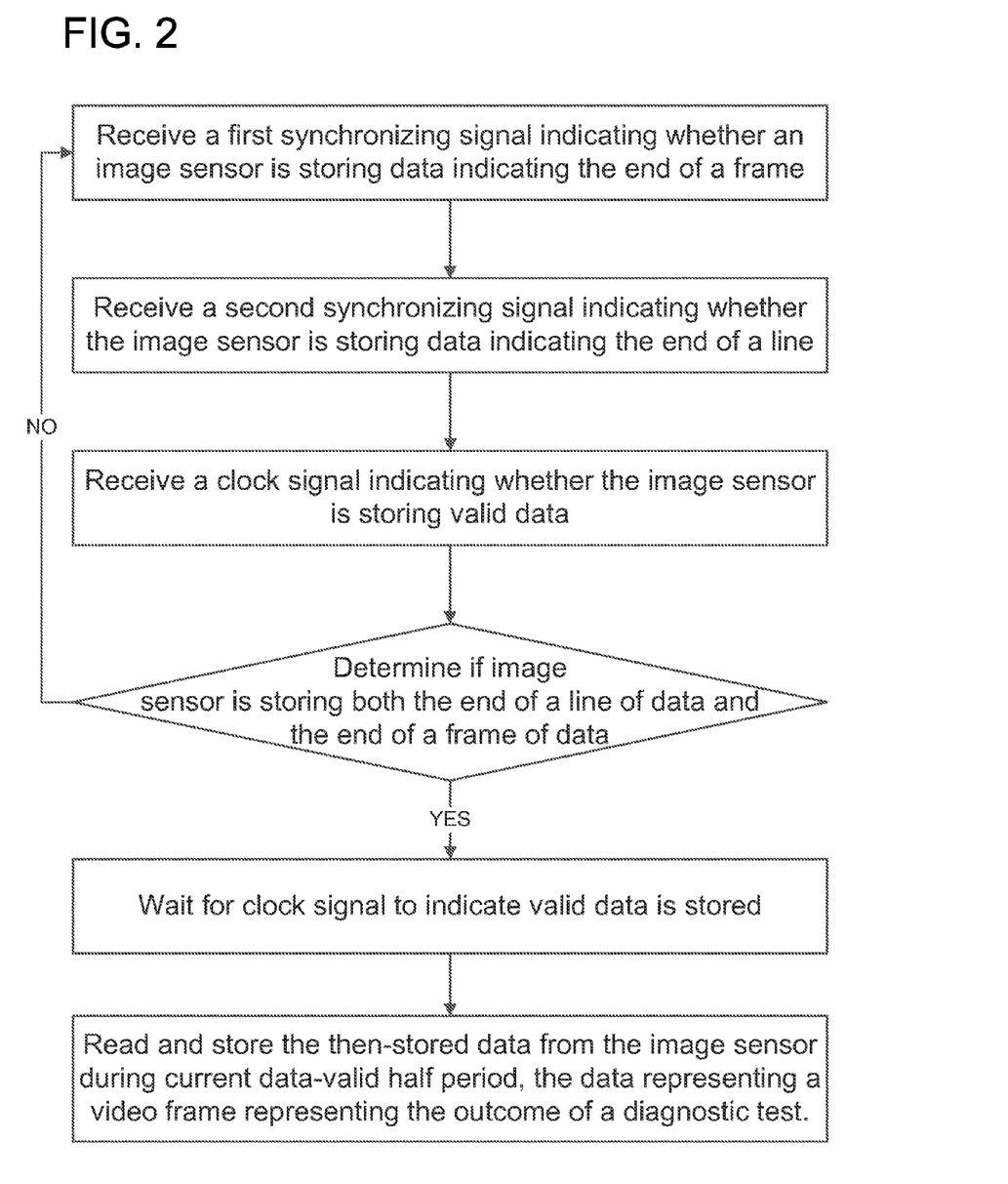
FIG. 2 is a flow diagram illustrating the steps performed by a microcontroller in one embodiment of the system disclosed herein.

The present disclosure provides video frame data receivers that are capable of image acquisition at low frame rates. While conventional video frame data receivers are capable of real-time video capture (e.g., 15 to 30 frame per second), they are inefficient for applications in which lower frame capture rates are desired. The video frame data receivers of the present disclosure may be used to capture images from diagnostic test or assays in which lower frame capture rates (e.g., approximately 5 frames per second or less) are desired including, for example, lateral flow test strips. The video frame data receivers of the present disclosure remove the need for a glue logic comprised of discrete components and lends itself to a wide range of microprocessors and microcontrollers lacking dedicated hardware camera interfaces. Accordingly, additional electronic components beyond the microcontroller and camera module are not necessary since the task of interfacing the camera and microcontroller is performed by the microcontroller's firmware.

The video frame data receivers of the present disclosure are preferably used with an immunoassay device including, for example, devices used to measure one or more analytes on an assay.

Exemplary assays contemplated for use with the methods of the present disclosure include lateral flow assay test strips. Lateral flow assay test strips may comprise a membrane system that forms a single fluid flow pathway along the test strip. The membrane system may include one or more components that act as a solid support for immunoreactions. For example, porous, bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on the solid support. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser may be used to stripe antibodies that bind the analyte of interest, including a labeled antibody conjugate, onto a glass fiber conjugate pad and a nitrocellulose strip. The test strip may or may not be otherwise treated, for example, with sugar to facilitate mobility along the test strip or with water-soluble non-immune animal proteins, such as albumins, including bovine (BSA), other animal proteins, water-soluble polyamino acids, or casein to block non-specific binding sites.

Any antibody, including polyclonal or monoclonal antibodies, or any fragment thereof, such as the Fab fragment, that binds the analyte of interest, is contemplated for use herein.

An antibody conjugate containing a detectable label may be used to bind the analyte of interest. The detectable label used in the antibody conjugate may be any physical or chemical label capable of being detected on a solid support using a reader, preferably a reflectance reader, and capable of being used to distinguish the reagents to be detected from other compounds and materials in the assay.

Suitable antibody labels are well known to those of skill in the art and include, but are not limited to, enzyme-substrate combinations that produce color upon reaction, colored particles, such as latex particles, colloidal metal or metal or carbon sol labels, fluorescent labels, and liposome or polymer sacs, which are detected due to aggregation of the label. In an embodiment, colloidal gold is used in the labeled antibody conjugate. The label may be derivatized for linking antibodies, such as by attaching functional groups, such as carboxyl groups to the surface of a particle to permit covalent attachment of antibodies. Antibodies may be conjugated to the label using well known coupling methods.

The assay test strip may be any conventional lateral flow assay test strip such as disclosed in EP 291194 or U.S. Pat. No. 6,352,862. The test strip may comprise a porous carrier containing a particulate labeled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors may then generate a current roughly proportional to the amount of light falling upon it. The amount of light reaching the photodetector depends upon the amount of colored particulate label present and therefore the amount of analyte. Thus the amount of analyte present in the sample may be determined. This method of optically determining the analyte concentration is described more fully in EP 653625.

A sample may include, for example, anything which may contain an analyte of interest. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

A fluid sample (e.g., biological fluid) may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642.

A sample may include, for example, anything which may contain an analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A liquid sample may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

An analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof (see, e.g., U.S. Pat. Nos. 4,366,241; 4,299,916; 4,275,149; and 4,806,311).

In an embodiment, a sample receiving zone on the surface of a lateral flow assay test strip accepts a fluid sample that may contain one or more analytes of interest. In an embodiment, the sample receiving zone is dipped into a fluid sample. A label zone is located downstream of the sample receiving zone, and contains one or more mobile label reagents that recognize, or are capable of binding the analytes of interest. Further, a test region may be disposed downstream from the label zone, and contains test and control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Thus, as the fluid sample flows along the matrix, the analyte of interest will first bind with a mobilizable label reagent in the label zone, and then become restrained in the test zone.

In an embodiment, the sample receiving zone may be comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber.

The sample receiving zone may be comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present invention also include those application pad materials disclosed in U.S. Pat. No. 5,075,078.

In a further embodiment, the sample receiving zone may be comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad.

In an embodiment, the label zone material may be treated with labeled solution that includes material-blocking and label-stabilizing agents. Blocking agents include, for example, bovine serum albumin (BSA), methylated BSA, casein and nonfat dry milk. Stabilizing agents are readily available and well known in the art, and may be used, for example, to stabilize labeled reagents.

The label zone may contain a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of test and control zones in the device, which allow for the accumulation of labeled reagent in designated zones.

The labeling zone may also include control-type reagents. These labeled control reagents often comprise detectable moieties that will not become restrained in the test zones and that are carried through to the test region and control zone(s) by fluid sample flow through the device. In a frequent embodiment, these detectable moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced.

The test region may include a control zone for verification that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest. In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form).

In an embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectable signal (e.g., be of the same color) or provide distinguishable detectable signals (e.g., have different colored labels or other detection systems) upon accumulation in the control zone(s).

In an embodiment, the labeled control reagent comprises a detectable moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

The use of a control zone is helpful in that appearance of a signal in the control zone indicates the time at which the test result can be read, even for a negative result. Thus, when the expected signal appears in the control line, the presence or absence of a signal in a test zone can be noted.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectable signal. Devices may incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones.

The test strip optionally may be contained within a housing for insertion into the reflectance reader. The housing may be made of plastic or other inert material that does not interfere with the assay procedure.

The lateral flow assay test strip may be suited for use with a reading device that comprises one or more of the following: a central processing unit (CPU) or microcontroller; one, two, or more LED's; one, two, or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay.

Any device which is compatible for use with an assay test strip, preferably a reflectance reader, for determining the assay result is contemplated for use herein. Such test strip devices as are known to those of skill in the art (see, e.g., U.S. Pat. Nos. 5,658,801, 5,656,502, 5,591,645, 5,500,375, 5,252, 459, 5,132,097). Reflectance and other readers, including densitometers and transmittance readers, are known to those of skill in the art (see, e.g., U.S. Pat. Nos. 5,598,007, 5,132, 097, 5,094,955, 4,267,261, 5,118,183, 5,661,563, 4,647,544, 4,197,088, 4,666,309, 5,457,313, 3,905,767, 5,198,369, 4,400,353).

It should be understood by those skilled in the art that various modifications, combinations, sub-combinations and alterations may occur depending on design requirements and other factors insofar as they are within the scope of the appended claims or the equivalents thereof.

The invention claimed is:

1. A video frame data receiver for capturing images from a diagnostic test or assay at a low capture rate, said video frame data receiver comprising:
   at least one microprocessor;
   at least one signal receiver; and
   at least one memory device, wherein the at least one memory device stores instructions which, when executed by the at least one microprocessor, cause the at least one microprocessor to operate with the at least one signal receiver to:
   (a) receive a first synchronizing signal from an image sensor in signal communication with said at least one microprocessor, said image sensor configured to store data indicative of a video frame, said first synchronizing signal indicating at least whether the image sensor is storing data indicative of an end of a video frame,
   (b) receive a second synchronizing signal from the image sensor, said second synchronizing signal indicating at least whether the image sensor is storing data indicative of an end of one of a plurality of lines of the video frame,
   (c) receive a clock signal from the image sensor, said clock signal indicating whether said image sensor is currently storing valid data indicative of at least a portion of the video frame,
   (d) at a first point in time, determine whether said first synchronizing signal indicates that the image sensor is storing data indicative of the end of at least the portion of the video frame,
   (e) at said first point in time, also determine whether said second synchronizing signal indicates that the image sensor is storing data indicative of the end of one of the plurality of lines of the video frame, and
   (f) if, at said first point in time, said first synchronizing signal indicates that the image sensor is storing data indicative of the end of the video frame and the second synchronizing signal simultaneously indicates that the image sensor is storing data indicative of the end of one of the plurality of lines of the video frame:
      (i) poll the clock signal until said clock signal indicates that said image sensor is currently storing valid data indicative of at least a portion of the video frame, and
      (ii) when the clock signal indicates that the image sensor is currently storing valid data indicative of at least a portion of the video frame, read and store the then-stored data indicative of at least the portion of the video frame from the image sensor during a current data-valid half-period, said video frame representing an outcome of the diagnostic test or assay.

2. The video frame data receiver of claim 1, wherein the image sensor operates asynchronously with respect to the at least one microprocessor.

3. The video frame data receiver of claim 2, wherein the image sensor operates asynchronously with respect to the at least one microprocessor because the image sensor is in signal communication with an external oscillator.

4. The video frame data receiver of claim 2, wherein the image sensor operates asynchronously with respect to the at least one microprocessor due to an external crystal.

5. The video frame data receiver of claim 1, wherein the image sensor operates synchronously with respect to the at least one microprocessor by utilizing a same clock signal generator as the at least one microprocessor.

6. The video frame data receiver of claim 5, wherein the same clock signal generator is a frequency-division circuit which is in signal communication with the at least one microprocessor and the image sensor, said frequency-division circuit being at least one selected from the group consisting of a pulse-width modulator and a programmable clock peripheral.

7. The video frame data receiver of claim 1, wherein the instructions cause the at least one microprocessor to poll the clock signal until said clock signal indicates that said image sensor is currently storing valid data indicative of at least a portion of the video frame by polling the clock signal until detecting at least one selected from the group consisting of a rising edge of said clock signal and falling edge of said clock signal.

8. The video frame data receiver of claim 1, which includes a general purpose input/output peripheral, and wherein the instructions cause the at least one microprocessor to operate with the general purpose input/output peripheral to read and store the then-stored data indicative of at least the portion of the video frame from the image sensor.

9. The video frame data receiver of claim 1, which includes an external memory interface, and wherein the instructions cause the at least one microprocessor to operate with the external memory interface to at least read the then-stored data indicative of at least the portion of the video frame from the image sensor.

10. The video frame data receiver of claim 9, wherein the external memory interface enables the at least one microprocessor to communicate with at least one selected from the group consisting of: a read only memory (ROM) unit, a flash memory unit, and a static random access memory (SRAM) unit.

11. The video frame data receiver of claim 1, wherein the instructions cause the at least one microprocessor to operate with the at least one signal receiver to repeat (a) to (f) a plurality of times.

12. A video frame data receiver for capturing images from a diagnostic test or assay at a low capture rate, said video frame data receiver comprising:
at least one microprocessor;
at least one signal receiver; and
at least one memory device, wherein the at least one memory device stores instructions which, when executed by the at least one microprocessor, cause the at least one microprocessor to operate with the at least one signal receiver to:
(a) receive a first synchronizing signal from an image sensor in signal communication with said at least one microprocessor, said image sensor configured to store data indicative of a video frame, said first synchronizing signal indicating at least whether the image sensor is storing data indicative of an end of a video frame,
(b) receive a second synchronizing signal from the image sensor, said second synchronizing signal indicating at least whether the image sensor is storing data indicative of an end of one of a plurality of lines of the video frame,
(c) receive a clock signal from the image sensor, said clock signal indicating whether said image sensor is currently storing valid data indicative of at least a portion of the video frame,
(d) detect an interrupt based on said clock signal, said interrupt indicating that said image sensor is currently storing valid data indicative of at least a portion of the video frame,
(e) upon detection of said interrupt, determine whether said first synchronizing signal indicates that the image sensor is storing data indicative of the end of the video frame and determine whether said second synchronizing signal indicates that the image sensor is storing data indicative of the end of one of the plurality of lines of the video frame, and
(f) if, upon detection of said interrupt, said first synchronizing signal indicates that the image sensor is storing data indicative of the end of the video frame and the second synchronizing signal indicates that the image sensor is storing data indicative of the end of one of the plurality of lines of the video frame, read and store the then-stored data indicative of the video frame from the image sensor during a current data-valid half-period, said video frame representing an outcome of the diagnostic test or assay.

13. The video frame data receiver of claim 12, wherein the image sensor operates asynchronously with respect to the at least one microprocessor.

14. The video frame data receiver of claim 13, wherein the image sensor operates asynchronously with respect to the at least one microprocessor because the image sensor is in signal communication with an external oscillator.

15. The video frame data receiver of claim 12, wherein the image sensor operates asynchronously with respect to the at least one microprocessor due to an external crystal.

16. The video frame data receiver of claim 12, wherein the image sensor operates synchronously with respect to the at least one microprocessor by utilizing a same clock signal generator as the at least one microprocessor.

17. The video frame data receiver of claim 16, wherein the same clock signal generator is a frequency-division circuit which is in signal communication with the at least one microprocessor and the image sensor, said frequency-division circuit being at least one selected from the group consisting of a pulse-width modulator and a programmable clock peripheral.

18. The video frame data receiver of claim 12, wherein the instructions cause the at least one microprocessor to detect an interrupt based on said clock signal by determining a feature of the clock signal selected from the group consisting of a rising edge and a falling edge of said clock signal.

19. The video frame data receiver of claim 12, which includes a general purpose input/output peripheral, and wherein the instructions cause the at least one microprocessor to operate with the general purpose input/output peripheral to read and store the then-stored data indicative of at least the portion of the video frame from the image sensor.

20. The video frame data receiver of claim 12, which includes an external memory interface, and wherein the instructions cause the at least one microprocessor to operate with the external memory interface to at least read the then-stored data indicative of at least the portion of the video frame from the image sensor.

21. The video frame data receiver of claim 20, wherein the external memory interface enables the at least one microprocessor to communicate with at least one selected from the group consisting of: a read only memory (ROM) unit, a flash memory unit, and a static random access memory (SRAM) unit.

22. The video frame data receiver of claim 12, wherein the instructions cause the at least one microprocessor to operate with the at least one signal receiver to repeat (a) to (f) a plurality of times.

23. A video frame data receiver for capturing images from a diagnostic test or assay at a low capture rate, said video frame data receiver comprising:
   at least one microprocessor;
   at least one signal receiver; and
   at least one memory device, wherein the at least one memory device stores instructions which, when executed by the at least one microprocessor, cause the at least one microprocessor to operate with the at least one signal receiver to:
   (a) receive a first synchronizing signal from an image sensor in signal communication with said at least one microprocessor, said image sensor configured to store data indicative of a video frame, said first synchronizing signal indicating at least whether the image sensor is storing data indicative of an end of one of a plurality of lines of the video frame,
   (b) receive a clock signal from the image sensor, said clock signal indicating whether said image sensor is currently storing valid data indicative of at least a portion of the video frame,
   (c) detect an interrupt based on said first synchronizing signal, said interrupt indicating that said image sensor is storing data indicative of the end of one of the plurality of lines of the video frame, and
   (d) upon detection of said interrupt:
      (i) determine whether the image sensor is currently storing valid data indicative of at least the portion of the video frame, and
      (ii) when the image sensor is currently storing valid data indicative of at least the portion of the video frame, read and store the then-stored data indicative of at least the portion of the video frame from the image sensor during a current data-valid half-period, said video frame representing an outcome of the diagnostic test or assay.

24. The video frame data receiver of claim 23, wherein the image sensor operates asynchronously with respect to the at least one microprocessor because the image sensor is in signal communication with an external oscillator.

25. The video frame data receiver of claim 23, wherein the image sensor operates synchronously with respect to the at least one microprocessor by utilizing a same clock signal generator as the at least one microprocessor.

26. The video frame data receiver of claim 25, wherein the same clock signal generator is a frequency-division circuit which is in signal communication with the at least one microprocessor and the image sensor, said frequency-division circuit being at least one selected from the group consisting of a pulse-width modulator and a programmable clock peripheral.

27. The video frame data receiver of claim 23, wherein the instructions cause the at least one microprocessor to detect an interrupt based on said first synchronizing signal by detecting at least one feature of the first synchronizing signal selected from the group consisting of a rising edge of said first synchronizing signal and a falling edge of said first synchronizing signal.

28. The video frame data receiver of claim 23, which includes a general purpose input/output peripheral, and wherein the instructions cause the at least one microprocessor to operate with the general purpose input/output peripheral to read and store the then-stored data indicative of at least the portion of the video frame from the image sensor.

29. The video frame data receiver of claim 23, wherein the instructions cause the at least one microprocessor to determine whether the image sensor is currently storing valid data indicative of at least the portion of the video frame by polling the clock signal to determine a data-valid edge of said clock signal.

30. The video frame data receiver of claim 29, wherein the data-valid edge of said clock signal is at least one selected from the group consisting of a rising edge of said clock signal and a falling edge of said clock signal.

31. The video frame data receiver of claim 27, wherein the instructions cause the at least one microprocessor to determine whether the image sensor is currently storing valid data indicative of at least the portion of the video frame by polling the clock signal to determine at least one feature of the clock signal selected from the group consisting of: a rising edge of the clock signal and a falling edge of the clock signal.

32. The video frame data receiver of claim 23, wherein upon determining that the image sensor is currently storing valid data indicative of the video frame, the instructions cause the at least one microprocessor to read the then-stored data indicative of the video frame from the image sensor within a time period equal to less than one-half of the period of the clock signal.

33. The video frame data receiver of claim 23, wherein the instructions cause the at least one microprocessor to determine whether the image sensor is currently storing valid data indicative of the video frame based on whether the clock signal is currently in a data-valid half-period.

34. The video frame data receiver of claim 33, wherein if the image sensor is currently storing valid data indicative of the video frame, the instructions cause the at least one microprocessor to read the then-stored data indicative of the video frame only during the current data-valid half-period and to read and store the then-stored data indicative of the video within a full period of the clock signal.

35. The video frame data receiver of claim 23, wherein the instructions cause the at least one microprocessor to operate with the at least one signal receiver to repeat (a) to (d) a plurality of times.

36. A video frame data receiver for capturing images from a diagnostic test or assay at a low capture rate, said video frame data receiver comprising:
   at least one microprocessor;
   at least one signal receiver; and
   at least one memory device, wherein the at least one memory device stores instructions which, when executed by the at least one microprocessor, cause the at least one microprocessor to operate with the at least one signal receiver to:
   (a) receive a first synchronizing signal from an image sensor in signal communication with said at least one microprocessor, said image sensor configured to store data indicative of a video frame, said first synchronizing signal indicating at least whether the image sensor is storing data indicative of an end of one of a plurality of lines of the video frame, (b) receive a clock signal from the image sensor, said clock signal indicating whether said image sensor is currently storing valid data indicative of at least a portion of the video frame,
(c) detect an interrupt based on said first synchronizing signal, said interrupt indicating that said image sensor is storing data indicative of the end of one of the plurality of lines of the video frame, and
(d) upon detection of said interrupt, read the then-stored data indicative of at least the portion of the video frame from the image sensor only during the current data-valid half-period due to an alignment of said execution of said instructions with said clock signal and thereafter store the then-stored data indicative of at least the portion of the video frame, during a current data-valid half-period, said video frame representing an outcome of the diagnostic test or assay.

37. The video frame data receiver of claim 36, wherein the instructions cause the at least one microprocessor to operate with the at least one signal receiver to repeat (a) to (d) a plurality of times.

\* \* \* \* \*